United States Patent [19]

Johnson et al.

[11] Patent Number: 4,952,518

[45] Date of Patent: Aug. 28, 1990

[54] AUTOMATED ASSAY MACHINE AND ASSAY TRAY

[75] Inventors: Larry J. Johnson, San Jose; Stephen R. Coates, Orinda; Rueyming Loor, Hercules, all of Calif.

[73] Assignee: Cetus Corporation, Emeryville, Calif.

[21] Appl. No.: 140,888

[22] Filed: Dec. 28, 1987

Related U.S. Application Data

[62] Division of Ser. No. 889,797, Jul. 24, 1986, abandoned, which is a division of Ser. No. 656,234, Oct. 1, 1984, Pat. No. 4,681,742.

[51] Int. Cl.$^5$ .................. G01N 33/543; G01N 35/02
[52] U.S. Cl. ...................... 436/518; 422/65; 422/73; 436/47; 436/531
[58] Field of Search .............. 436/518, 531, 47, 857, 436/859; 422/65, 73, 100, 102, 109

[56] References Cited

U.S. PATENT DOCUMENTS

| | | | |
|---|---|---|---|
| 3,536,449 | 10/1970 | Astle | 73/863.32 X |
| 4,265,855 | 5/1981 | Mandle et al. | 422/65 |
| 4,478,094 | 10/1984 | Salomaa et al. | 73/863.32 |
| 4,536,369 | 8/1985 | Sakurada et al. | 422/65 |
| 4,554,839 | 11/1985 | Hewett et al. | 73/863.32 X |

*Primary Examiner*—Michael S. Marcus
*Attorney, Agent, or Firm*—Skjerven, Morrill, MacPherson Franklin & Friel

[57] ABSTRACT

A machine for transferring liquids to and from the wells of assay trays in a controlled, automated manner and a solid phase assay tray for use with the machine. The machine includes a horizontally translatable table (15) that holds the tray (46), a plurality of liquid dispensing manifolds (54) for dispensing liquids into the tray wells (50) and an aspirating manifold (65) for aspirating liquid from the well. The dispensing and aspirating manifolds are mounted on a vertically translatable head (16) above the table. Each dispensing manifold is equipped with a row of dispensing tubes (56) and is connected via a pump (58) to a liquid container (62). The aspirating manifold is equipped with a row of aspirating tubes (66) and is connected via a pump (69) to a waste liquid receptacle (73). A microprocessor (85) controls the movements of the table and manifolds and operates the pumps. The tray wells include means, such as sloping bottoms (74) or subwells (83), that cause the solid phase (76) to occupy a particular position in the wells and sumps (75), (84) that are positioned relative to the location of the solid phase such that they may be accessed vertically by the aspirating tubes without danger of disturbing the solid phase. The bottoms of the sumps have optically flat areas so that beams of light may be passed vertically through the liquid contents of the wells without intersecting the solid phase to make optical measurements of the liquid contents.

4 Claims, 5 Drawing Sheets

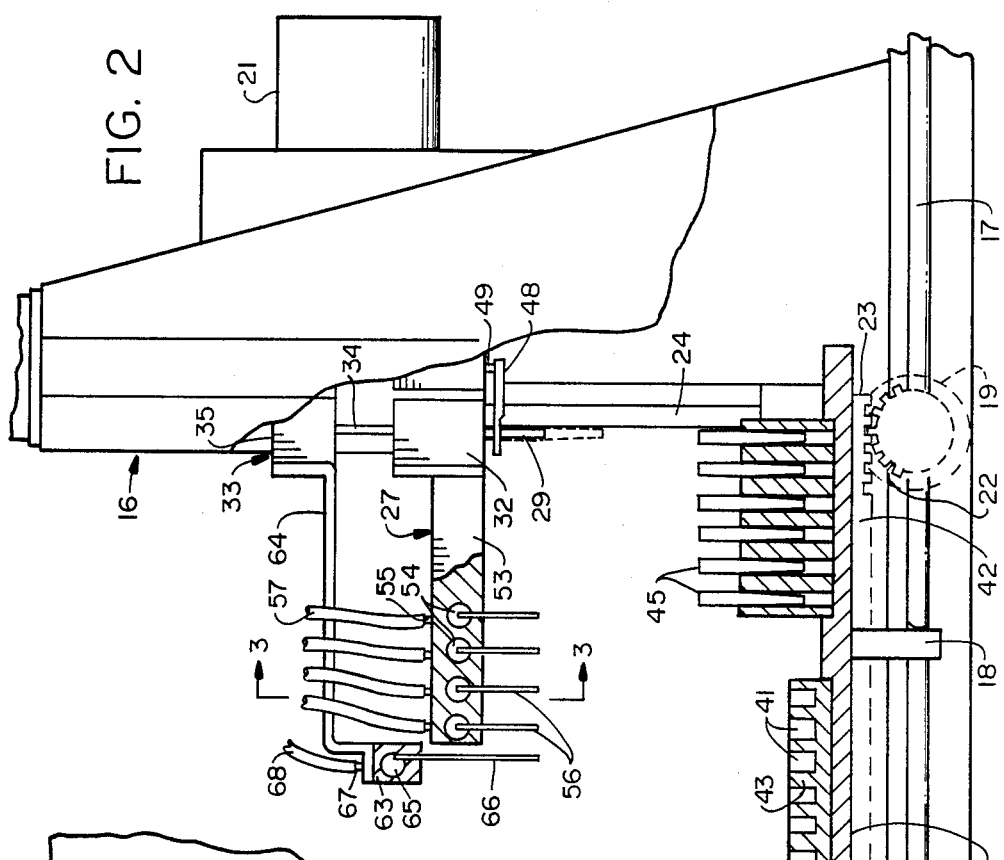
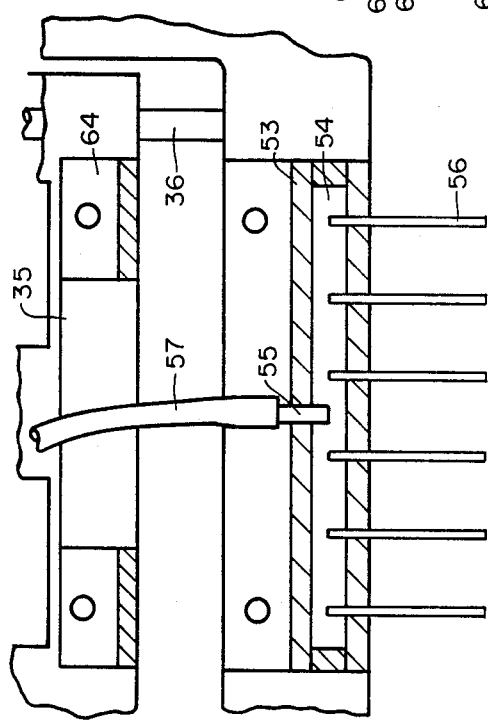
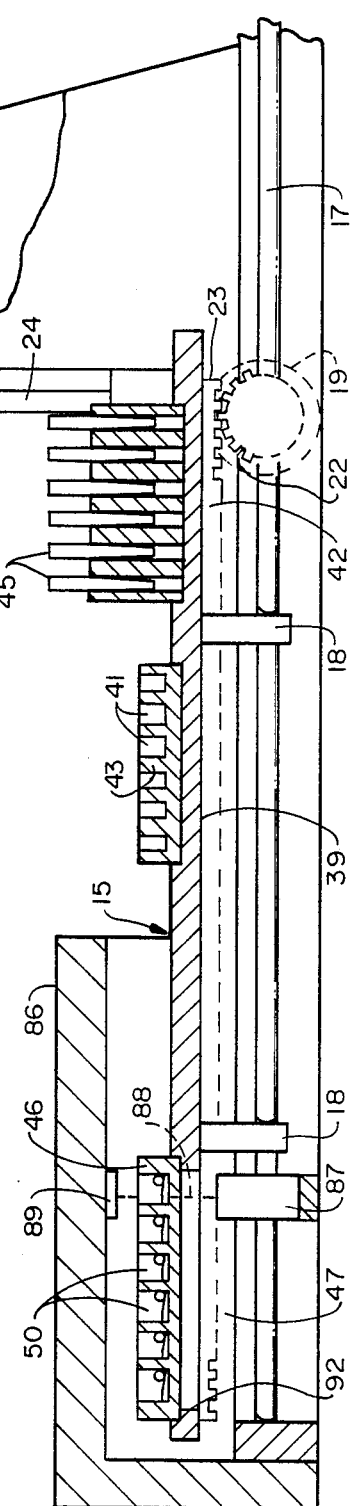
FIG. 2
FIG. 3

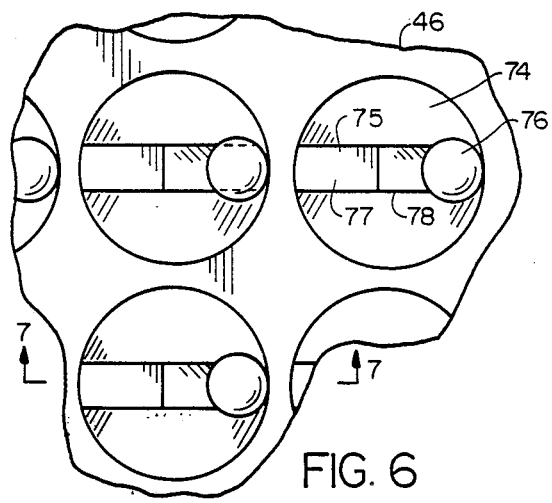
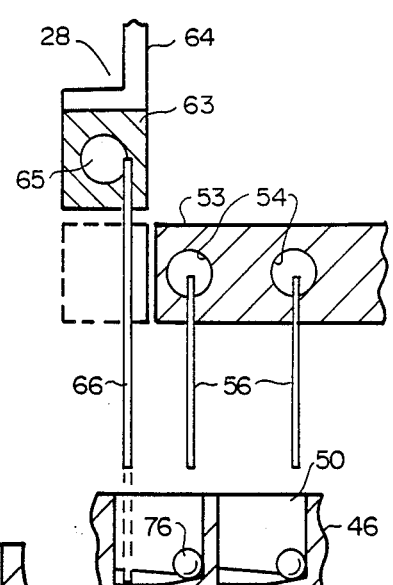
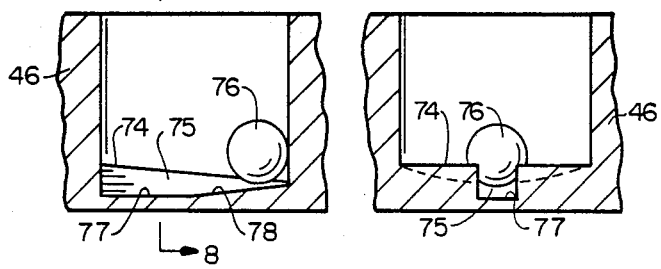
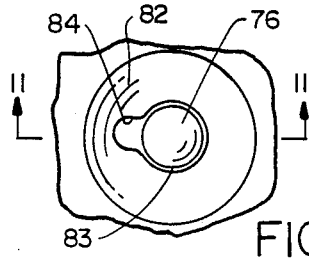
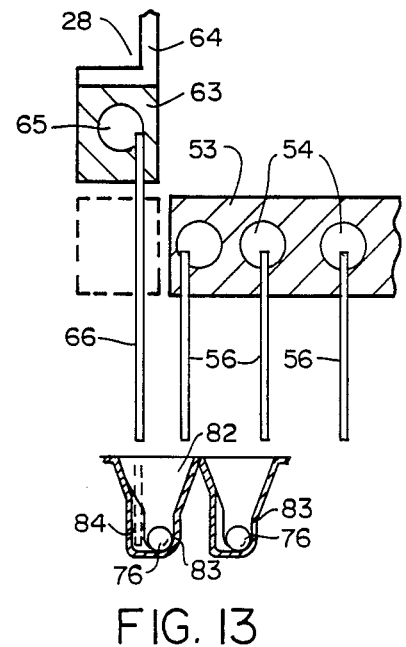
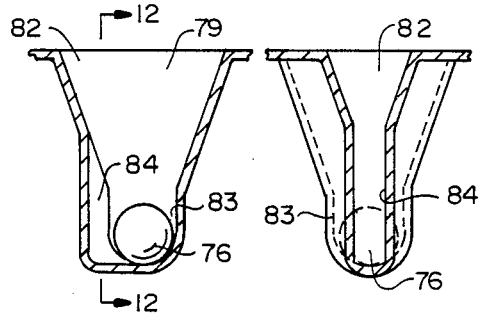

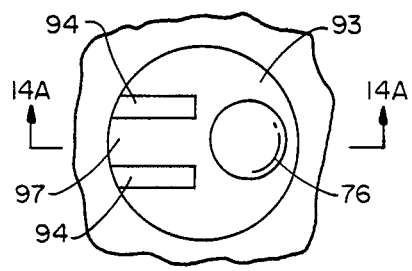
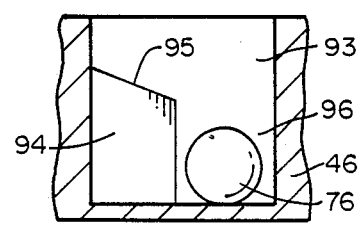
FIG. 14  FIG. 14A
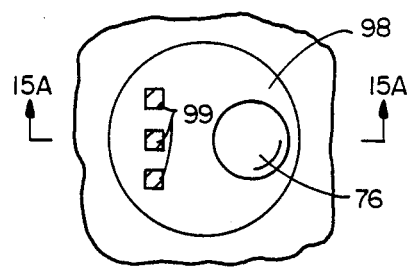
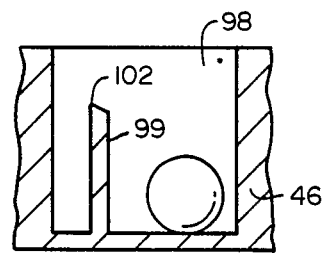
FIG. 15  FIG. 15A
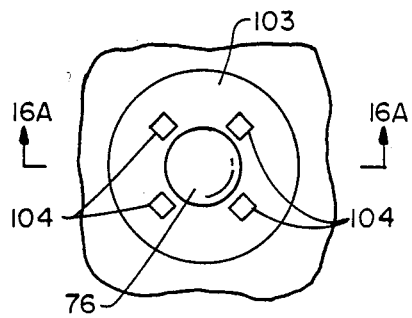
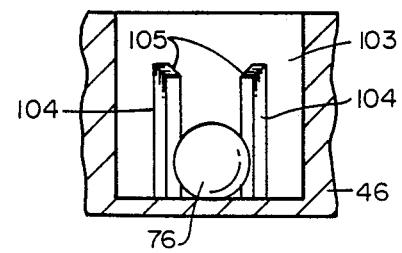
FIG. 16  FIG. 16A
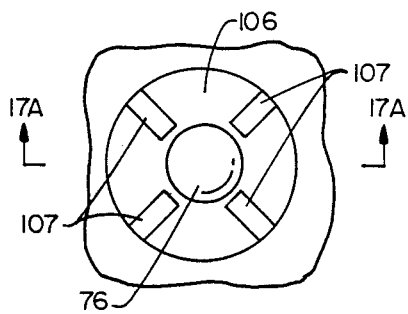
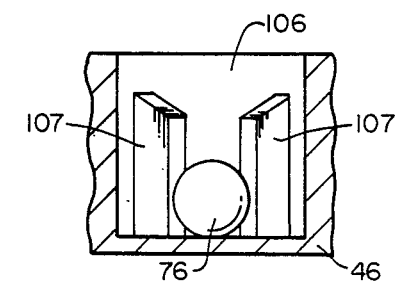
FIG. 17  FIG. 17A

4,952,518

AUTOMATED ASSAY MACHINE AND ASSAY TRAY

This application is a division of application Ser. No. 889,797, filed July 24, 1986 abandoned, which is a division of application Ser. No. 656,234, filed Oct. 1, 1984 now U.S. Pat. No. 4,681,742.

DESCRIPTION

1. Technical Field

This invention is in the field of immunoassay apparatus. More particularly it concerns (a) an immunoassay tray for carrying out an immunoassay in which an immunochemical is fixed to a solid phase and the immunochemical-bearing solid phase is incubated with liquid reagents and washed with wash liquids and (b) a machine for use in combination with the tray for depositing and withdrawing the reagent/wash liquids from the tray wells.

2. Background Art

Immunoassays are used to detect the presence or quantity of a given immunochemical in a sample suspected of containing the immunochemical. Most immunoassays involve the formation of immune complexes via antigenantibody binding. The complexes are detected in various ways, such as by labels bound directly or indirectly to the complex.

Many immunoassays require that the complexes be subjected to one or more isolations, washings, and treatments with liquid reagents. In order to facilitate handling the immune complexes, one of the components of the complex is used in a solid phase form (i.e., immobilized on a particulate immunosorbent material) which results in the complexes also being in solid phase. The immobilized complexes may be easily washed, incubated with additional reagents, and isolated as required by the particular type of assay. Assays that employ a particulate solid phase reagent are commonly referred to as "solid phase", "heterogeneous", or "immunosorbent" assays. For convenience they will be referred to herein as "solid phase" immunoassays.

Solid phase assays are frequently carried out in assay trays or tubes. Assay trays are plates that have a plurality of wells (usually 20, 24, 48 or 96) arranged in rows and columns into which the particulate solid phase is placed and treated sequentially with the liquid reagents and washes involved in the particular assay. Various well configurations have been used or suggested, including wells having flat bottoms, V-shaped bottoms, and U-shaped bottoms. The liquid reagents and washes are normally added and withdrawn from the wells with manual, semiautomated or automated pipettes.

With most of the current assay trays the location of the solid phase in the well bottom is happenstance. Accordingly, when the pipette tip is inserted into the well there is a possibility of hitting the solid phase and mechanically dislodging bound materials from its surface. Also, the solid phase may interfere with withdrawing liquids completely from the well. In view of this, many assay protocols require that the solid phase be removed from the wells prior to liquid transfer and replaced in the wells after liquid transfer. Also in some types of assays, such as fluorescent immunoassays (FIAs) and enzyme immunoassays (EIAs), the reading step of the assay involves passing a beam of light through the liquid phase. If the solid phase is positioned randomly in the wells it may interrupt the path of the beam, requiring adjustment of the beam path or removal of the solid phase from the well.

Manual, semiautomated or automated pipettes are commonly used for the liquid transfer steps of immunoassays. An example of a fully automated pipette system that may be used to carry out an immunoassay is described in commonly owned U.S. application Ser. No. 06/489,866, filed May 5, 1983. The extensive number of steps and reagents involved in many immunoassays may, however, make it impractical to use such systems where the reagents are carried in open receptacles on a moving table and are transferred via pipette. Also, these pipette systems are generally not capable of carrying out the reading phase of an immunoassay. The investigator must, therefore, transfer the assay tray to reading apparatus. In sum, current assay equipment requires substantial human intervention and is not capable of conducting assays from start-to-finish automatically.

Among the objects of the present invention are to provide a novel assay tray whose wells include means for positioning the solid phase such that it does not interfere with the implement(s) used to introduce and withdraw liquid from the wells or optical measurements made on the liquid contents of the well at the end of the assay and a machine that introduces and withdraws liquids from such wells in an automatic, controlled fashion without necessarily using pipettes and can be adapted to carry out assays automatically from start-to-finish.

Use of the trays of the invention avoids handling of the solid phase, improves the reliability of the assay, and permits solid phase assays to be conducted automatically. The invention machine is particularly adapted to be used in combination with the trays and provides a means for carrying out solid phase assays from start-to-finish with no or only minimal operator monitoring and intervention. In this regard the machine may be readily equipped to conduct the reading phase of the assay automatically and to communicate with a microprocessor to record assay data, correlate such data with other data (if necessary or desired), process or analyze the data, and prepare reports based on the data. When equipped with assay reading means and linked to a microprocessor programmed with suitable software, the present invention provides a self-contained system for conducting, recording, and reporting assays.

STATEMENT OF THE INVENTION

There are two principal aspects of the invention: (1) novel assay trays for use in solid phase assays and (2) a machine for supplying and withdrawing liquid reagents to and from the wells of assay trays in an automated controlled manner. These aspects are broadly described below.

The assay trays are used in assays wherein a a particulate solid phase, typically carrying an immobilized reagent, is contacted with one or more liquids. They include means for positioning the solid phase at a predetermined location in the wells combined with other novel structural features that permit liquid to be aspirated from the wells without disturbing the solid phase or the solid phase to be immersed in a minimal volume of liquid or facilitate automated reading of the liquid in the wells.

Thus, in one embodiment the invention tray comprises a plate having a plurality of wells for receiving the solid phase and liquids, the wells having:

(a) a solid phase positioning means for positioning the solid phase in a predetermined location in the wells; and (b) a sump means spaced from the location of the solid phase whereby liquid may be withdrawn from the wells without disturbing the solid phase.

In another embodiment the invention tray comprises a plate having a plurality of wells for receiving the solid phase and the liquids, the wells each having:

(a) a subwell section for holding the solid phase, the size and shape of the subwell section being such that the solid phase may be immersed in the subwell section in a small volume of liquid; and (b) a main well section of substantially greater cross sectional area and volume than the subwell section.

The machine comprises in combination:

(a) a head assembly translatable between upper and lower positions along a vertical axis and including:

(i) at least one liquid reagent dispensing manifold having an inlet adapted to be connected to one or more liquid reagent sources and a plurality of spaced outlets each fitted with a vertically depending liquid reagent dispensing tube, the spacing between the dispensing tubes being in correspondence with the spacing between the wells of the assay tray; and (ii) at least one liquid reagent aspirating manifold having an outlet and a plurality of spaced inlets each fitted with a vertically depending liquid reagent aspirating tube, the spacing between the aspirating tubes being in correspondence with the spacing between the wells of the assay tray;

(b) dispensing pump means operably associated with the source(s) of liquid reagent and the dispensing manifold inlet(s) for pumping liquid reagent from the source(s) into the dispensing manifold(s) whereby liquid reagent is deposited in the wells;

(c) aspirating pump means operably associated with the outlet(s) of the aspirating manifold(s) for creating a vacuum therein whereby liquid reagent is aspirated from the wells;

(d) means for moving the head assembly along its vertical axis;

(e) a table mounted beneath the head and being adapted to carry the assay tray, the table and/or head being moveable horizontally relative to one another;

(f) means for moving the table and/or head horizontally to position the rows of wells in registry with the dispensing tubes and aspirating tubes; and (g) means for controlling each of the moving means for the head and table, the dispensing pump means, and the aspirating pump means whereby predetermined volumes of liquid reagents are deposited and aspirated from the wells in a predetermined sequence.

BRIEF DESCRIPTION OF THE DRAWINGS

In the drawings:

FIG. 2 is a partly sectional, partly broken-away side elevational view of the machine of FIG. 1, showing the head assembly of the machine in its upper position;

FIG. 3 is an enlarged sectional view taken in the direction of arrows 3—3 of FIG. 2;

FIG. 6 is an enlarged top view of a portion of the assay tray shown in FIG. 1;

FIG. 7 is a sectional view taken in the direction of arrows 7—7 of FIG. 6;

FIG. 8 is a sectional view taken in the direction of arrows 8—8 of FIG. 7;

FIG. 9 is a sectional, partly schematic view of a portion of the machine of FIG. 1 showing the operation of the liquid withdrawal mechanism of the machine;

FIG. 10 is an enlarged top view of a portion of a second embodiment of the assay tray;

FIG. 11 is a sectional view taken in the direction of arrows 10—10 of FIG. 10;

FIG. 12 is a sectional view taken in the direction of arrows 12—12 of FIG. 11;

FIG. 13 is a sectional, partly schematic view corresponding to FIG. 9 showing the operation of the machine to withdraw liquid from the assay tray of FIG. 10.

FIG. 14 is an enlarged top view of a portion of a third embodiment of the assay tray;

FIG. 14a is a sectional view taken in the direction of arrows 14—14 of FIG. 14;

FIG. 15 is an enlarged top view of a portion of a fourth embodiment of the assay tray;

FIG. 15a is a sectional view taken in the direction of arrows 15—15 of FIG. 15;

FIG. 16 is an enlarged top view of a portion of a fifth embodiment of the assay tray;

FIG. 16a is a sectional view taken in the direction of arrows 16—16 of FIG. 16;

FIG. 17 is an enlarged top view of a portion of a sixth embodiment of the assay tray; and FIG. 17a is a sectional view taken in the direction of arrows 17—17 of FIG. 17.

MODES FOR CARRYING OUT THE INVENTION

Figure 1:
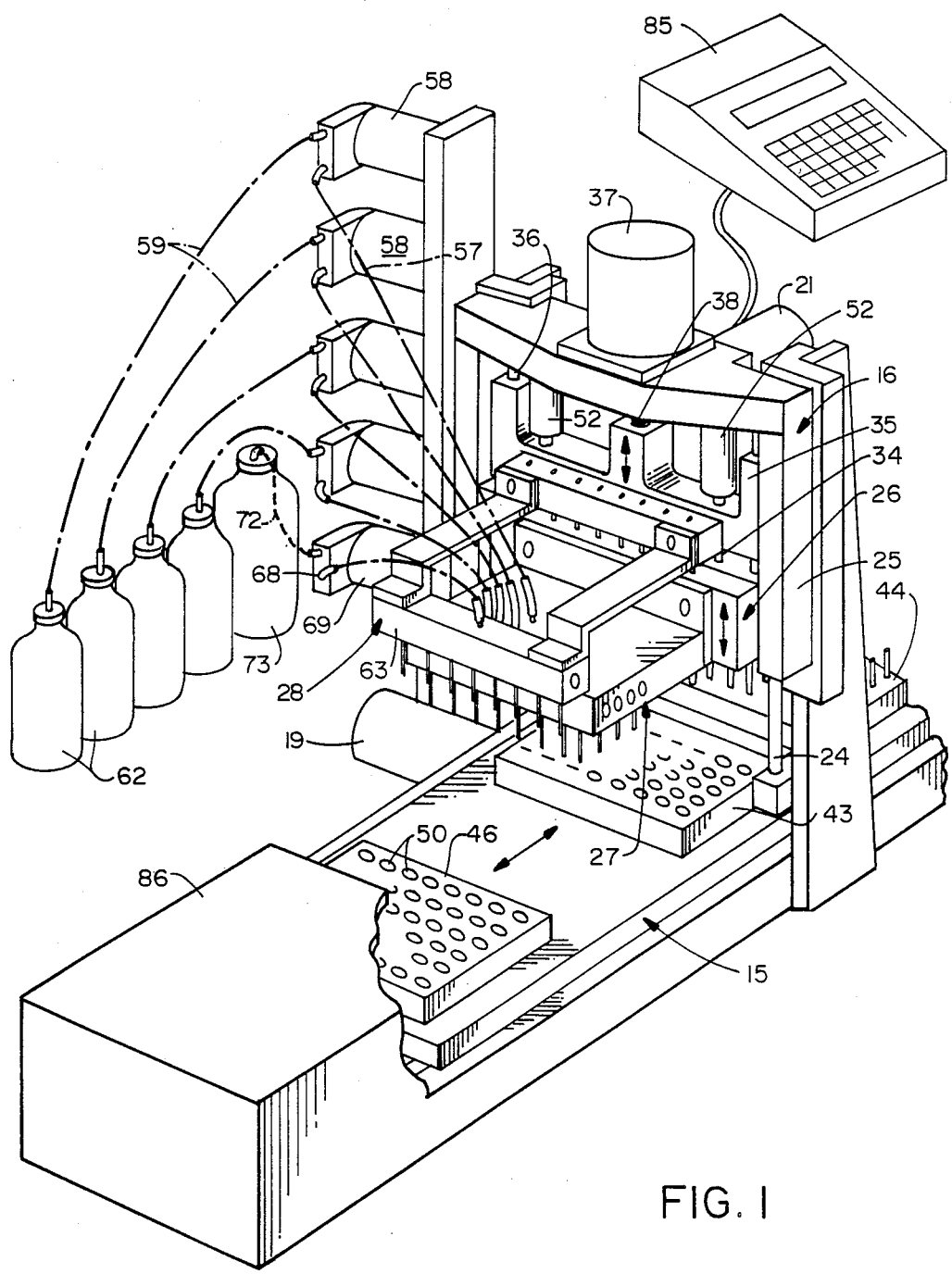
FIG. 1 is a perspective, partly broken-away view of a prototype embodiment of the assay machine of the invention.
Figures 4, 5:
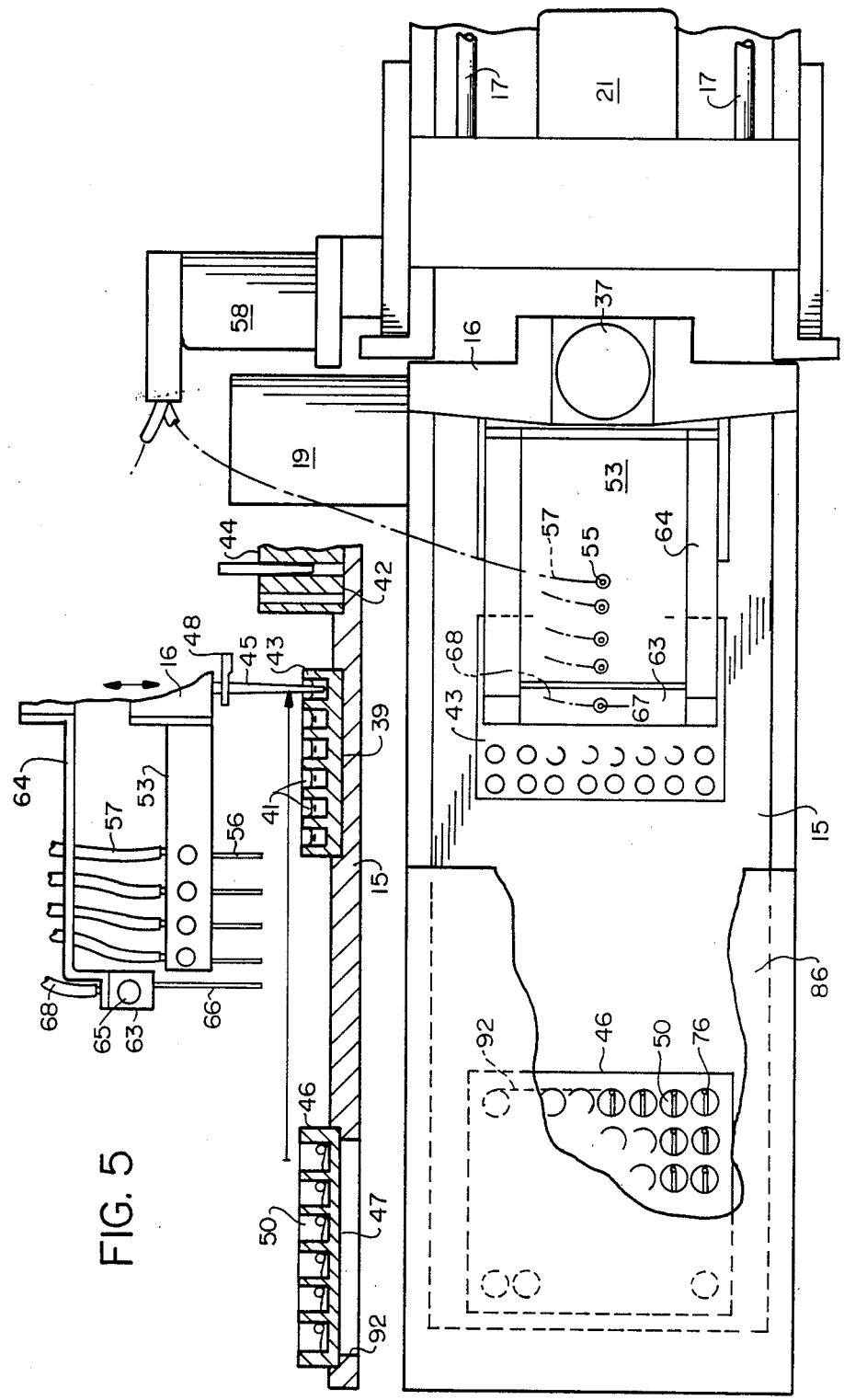
FIG. 4 is a partly broken-away top view of a portion of the machine of FIG. 1.
FIG. 5 is a sectional, side elevational view of a portion of the machine of FIG. 1 showing the head assembly of the machine in its lower position.

The tray and machine are especially useful for conventional solid phase immunoassays. It will be appreciated, however, that the invention may be used for assays or heterogeneous reactions that involve physical and/or chemical interactions or reactions between substances other than immunochemicals. The particular trays and machine shown in the drawings are designed to carry out enzyme immunoassays (EIAs), radioimmunoassays (RIAs), chemiluminescent immunoassays (CIAs) or fluorescent immunoassays (FIAs) in which the solid phase is a bead of an immunosorbent material.

The machine, which is best illustrated in FIGS. 1, 2, 4 and 5, is a modification of the machine that is described in copending, commonly owned U.S. application SER. No. 06/489,866, filed May 5, 1983. Referring to those Figures, the present machine includes two main movable parts: a horizontally translatable table 15 and a vertically translatable head assembly 16. The table 15 is mounted on hardened guide rods 17 by means of slide bearings 18. The table is translated horizontally by action of a stepper motor 19 through a pinion gear 22 connected to the motor and a rack 23 mounted on the underside of the table. Head assembly 16 is mounted for vertical movement on guide rods 24 by means of slide bearings 25. Translation of the head assembly is provided by a stepper motor 21 via a similar pinion gear-rack arrangement or lead screw mechanism (not shown).

Head assembly 16 supports three main subassemblies: a pipette and plunger subassembly 26; a dispensing manifold subassembly 27; and an aspirating manifold subassembly 28. These three subassemblies are the parts of the machine that introduce liquids into the assay tray wells and withdraw liquids therefrom. The pipette subassembly is an optional feature of this machine and is useful when it is necessary or desirable to be able to transfer precise amounts of liquid reagents to and from the tray. The details of the structure and function of the pipette subassembly are described in said copending application Ser. No. 06/489,866, which disclosure is incorporated herein by reference. In view of this, only a brief description of this subassembly follows.

The pipette subassembly includes a series of pipettes 29 (FIG. 2) that are arranged in a row transverse to the axis of translation of table 15. The pipettes are removably attached to the head assembly by means of a mounting block 32. A plunger mechanism 33 is mounted on the head assembly for vertical movement relative to the pipettes. The plunger mechanism includes a series of plunger rods 34, one being disposed respectively within each pipette. All of the rods are mounted on a common actuator bar 35 for concurrent vertical movement. The bar 35 is translated along guide rods 36 by means of a stepper motor 37 and a lead screw drive mechanism 38. Translation of the plunger rods relative to the pipettes changes the internal air volumes of the pipettes, causing a similar liquid volume to be aspirated into or expelled from the pipette tips 45.

The table 15 includes two work stations 39 and 42 for respectively accommodating two trays 43, 44. Tray 43 is a conventional titer tray that includes a matrix arrangement of wells 41 for housing the liquid(s) to be taken up by the pipette tips. Instead of a matrix of wells, tray 43 may be provided with one or more troughs that provide common liquid reservoirs from which liquid may be taken up. Tray 44 at the rear work station 42 can be a tip tray that contains a similar arrangement of receptacles that accommodate disposable pipette tips 45. The tips 45 are inserted onto and engage the respective ends of the pipettes 29 when the head assembly 16 is lowered by the stepper motor 21 after the table 15 has brought one row of tips 45 into registry with the pipettes.

Once the tips are in place on the pipette ends, the table is translated such that the pipettes are above and in registry with a row of wells in tray 43 that contains the liquid to be taken up into the tips. Instead of wells, tray 43 may have a common trough-like receptacle into which the tips are lowered. The tips are then lowered into the wells by translation of the head assembly and the tips are actuated by the plunger mechanism to withdraw a predetermined volume of liquid from the wells. The tips are then withdrawn from the wells by upward translation of the head assembly. As shown schematically in FIG. 5, the table is then translated to bring assay tray 46 positioned at work station 47 of the table below and in registry with the tips. The tips are lowered by downward translation of the head assembly into the wells 50 of tray and the fluid is ejected by actuation of the plunger mechanism of the pipette subassembly. If desired, the pipette operation may be repeated to extract more or other liquids from the titer tray and deposit it/them in the assay tray wells, with or without replacement of the tips, as desired.

Removal of the tips 45 from the pipettes is accomplished with a tip ejector means. The tip ejector means includes a stripper plate 48 that is best illustrated in FIG. 2. The plate has openings that accommodate the pipettes. The plate 48 is connected to and supported by a pair of vertically translatable rods 49 mounted on the head assembly 16. These rods are translated by means of a pair of solenoids 52 mounted on the head assembly. When the solenoids 52 are deactuated, the ejector plate 48 is maintained in its upper position. Actuation of the solenoids moves the plate vertically downward, to push the tips 45 down and release them from their frictional engagement with the ends of the pipettes 29.

The dispensing manifold subassembly 27 is used to introduce liquids into the wells 50 of the assay plate 46 except in instances where it is necessary or desirable to introduce the liquid via pipette tip because of the availability of the liquid reagent or the need for precise volume control. It is best shown in FIGS. 1, 2, and 3. It comprises a manifold block 53 that is mounted on the front of the head assembly such that it extends outwardly therefrom parallel to and above table 15. The block 53 contains a plurality of horizontally spaced, parallel chambers 54 for receiving the various liquids that are introduced into the wells according to the protocol of the assay being conducted. The spacing between the vertical center lines of the chambers is the same as the spacing between the center lines of the rows of wells in the assay tray. Referring to FIG. 3, each chamber has a single inlet in its upper wall fitted with a tubular sleeve 55 and a plurality of equispaced outlets (six in the depicted manifold) each fitted with a liquid dispensing tube 56 that extends vertically through the bottom wall of the block into a chamber 54. Pressure tight conduits 57 are pressure fit over the outer end of each sleeve 55 and extend therefrom to the exhaust ports of peristaltic (or similar fixed displacement pump) pumps 58. The inlet ports of the pumps are connected via another set of conduits 59 (FIG. 1) to containers 62 that hold the liquids that are used in the assay.

If expensive reagents are involved it will be desirable to use alternate assemblies of liquid containers and pumps that minimize dead volume. Such assemblies would involve a minimum of fluid passageways between the liquid reservoir and manifold. For instance self-contained syringe pump units mounted directly on the head assembly and stepper motors to drive the syringe plungers might be employed. Accordingly, as used in the claims the term "pump means" is intended to denote any device or mechanism that exerts the pressure (or suction in the case of aspiration) required to effect the desired liquid transfer.

Aspirating manifold subassembly 28 is the part of the machine that is used to withdraw liquid from the wells of the assay tray as required by the assay protocol. It includes an aspirating manifold block 63 mounted on the front of actuator bar 35 by means of arms 64 such that it is normally located outwardly and above the leading end of the dispensing manifold block 53. The aspirating manifold block contains a single chamber 65 that has a plurality of equispaced inlets each fitted with a liquid aspirating tube 66. These tubes are longer than the dispensing tubes 56 so that when the dispensing and aspirating manifold blocks are in their uppermost positions the distal ends of tubes 56 and 66 lie in a horizontal plane (FIGS. 9 and 13). The spacing between the tubes 66 is the same as the spacing between the center lines of the columns of wells in tray 46. The spacing between tubes 66 and the first row of dispensing tubes 56 along the axis of translation of table 15 is less than the diameter of the assay tray wells so that they may be positioned simultaneously in the same row of wells 50. Chamber 65 has a single outlet fitted with a sleeve 67. A pressure tight conduit 68 is fit over the outer end of sleeve 67 and extends to the inlet port of a peristaltic (or other fixed displacement pump) pump 69. The outlet port of pump 69 is connected via another conduit 72 to a receptacle 73 for receiving liquids withdrawn from the assay tray wells.

FIGS. 6-17a illustrate the structure of the assay tray wells and their relationship to the liquid dispensing and aspirating tubes. The wells shown in FIGS. 6-8 are cylindrical depressions, each of which has the same structure. Each well has a flat, sloping bottom wall 74 that has a diametrical slot 75 in it. The slope of wall 74 and slot 75 both serve to cause the solid phase used in the assay, in this case spheres or "beads" 76, that are placed in the wells to assume by gravity uniform and relatively fixed positions. In this regard, the width of the slot 75 is less than the diameter of the bead so that the latter cannot slip down into the slot. As shown the bead always assumes a resting position seated in the slot at the low end of the sloping bottom wall. The bottom of the slot includes a section 77 that is parallel to the bottom wall of the tray and spaced horizontally from the low end of the bottom wall of the well and an upwardly sloping section 78 that is generally beneath the position normally occupied by the bead. Slot 75 has several functions. First, it provides a seat for the bead. Second, it provides a drain or sump for liquid that may be accessed vertically by the aspirating tubes 66 without disturbing the bead. Third, section 77 provides an optically flat surface through which light may be transmitted in a vertical path that does not intersect the bead in order to carry out optical measurements on the liquid contents of the well. It will be appreciated that the portion of section 77 that provides an optical surface need not be flat but may define a lens or filter for focussing or otherwise altering the light passing through it.

The well 79 depicted in FIGS. 10-13 differs structurally from the well 50 of FIGS. 6-9, but functions in the same manner. This well consists of three sections: (a) an upper main well section 82, (b) a centrally located subwell 83 that provides a receptacle for the bead, and (c) a sump section 84. Each of the three sections opens into the other. Upper section 82 forms the mouth of the well and is generally frustoconical in shape, diverging outwardly directly from the interface with and opening of the subwell. Its shape causes the bead to drop into the subwell 83 when the bead is placed in the well. The frustoconical shape of the main section also facilitates the flow of liquid through the subwell during washing steps and provides a sufficiently large liquid surface to permit overhead fluorescent reading of the liquid contents of the well. In this regard, the minimum diameter for FIA reading is approximately 8 mm. The diameter of the main well section at its mouth will usually range between 15 and 20 mm. The subwell is generally cyclindrical in shape. Its diameter is less than the average diameter of section 82 but greater than the diameter of the bead. Standard bead sizes are 4.4, 6.4 and 8 mm. Accordingly the mean diameter of the subwell normally will range between 6 and 10 mm depending on the size bead it is intended to hold. Preferred sizes are: 10 mm diameter for 8 mm bead; 8 mm for 6.4 mm bead and 6 mm for 4.4 mm bead. It has a concave shaped bottom wall. Sump section 84 is in the form of an elongated slot whose width and thickness are less than the diameter of the bead so that the bead cannot fit into it. It is at least as deep as the subwell 83 so that liquid can freely drain into it from the subwell. The bottom wall of the sump is flat and parallel to the bottom wall of the tray. The configuration of the well 79 serves the same function as that of well 50, with an additional advantage. The frustoconical shape of main section 82 and the bead receptacle section combine to serve as a bead positioning means. Sump section 84 provides a fluid drainage area that may be accessed vertically without danger of disturbing the bead. The bottom wall of the sump section provides an optically flat surface for transmitting light through the fluid contents of the well without intersecting the bead. The configuration and size of the subwell permit the bead to be immersed with a relatively small volume of liquid. In this regard the volume of the subwell will normally be 30% or less of the volume of the entire well, usually 10% to 25% of the entire well. In general, the minimum volume of liquid to immerse the above described standard beads in the subwell will depend upon the size of the bead and diameter of the subwell. In the case of the above standard sized beads and using a subwell diameter about 1-2 mm larger than the bead diameter, the minimum volume will be about 200 to 500 $\mu$l. This ability to immerse the solid phase in a minimum volume of liquid is important when the assay protocol calls for use of expensive reagents. At the same time the upper liquid reservoir section allows the use of larger volumes of liquid such as are typically used in washing the solid phase.

FIGS. 14 and 14a show a well 93 that has a pair of axial spaced ribs or pillars 94 having sloping flat top surfaces 95. The ribs define a ramp that causes the bead to drop into a bead receptacle section 96 of the well. The space 97 between the ribs is less than the bead diameter and defines a sump area that may be accessed vertically without disturbing the bead.

FIGS. 15 and 15a and 16 and 16a depict trays in which the solid phase positioning means is a plurality of spaced vertical posts positioned strategically in the wells. The well 98 of FIGS. 15 and 15a has three axially elongated posts 99 with sloping top walls 102. The posts are aligned chordally and the distances between the posts and between the posts and the near portion of the cylindrical wall of the well is substantially less than the diameter of the bead. When a bead is dropped into the well this spacing and the sloping top walls 102 cause the bead to be positioned eccentrically in the well. The space between the posts and the near portion of the cylindrical well wall defines the sump area of the well. FIGS. 16 and 16a show a well 103 that has four vertical posts 104. The posts are positioned in the four quadrants of the well and have top surfaces 105 that slope downwardly toward the center of the well. This arrangement of wells causes the bead to be positioned centrally in the well. Sump areas are located between the posts and the cylindrical wall of the well.

FIGS. 17 and 17a depict a well configuration that is similar conceptually to the well of FIGS. 16 and 16a. The well 106 of FIGS. 17 and 17a has four radial ramps or fins 107 instead of the four posts 104 of well 103. The top walls of fins 107 slope downwardly toward the center of the well, again causing the bead to be positioned centrally. Sump areas are located between the fins. The bottom walls of each of wells 93, 98, 103, and 106 are flat so as to provide a flat surface through which a light beam may be passed vertically in a path that does not intersect the bead.

The operations of pumps 58, 69, stepper motors 19, 21, 37 and solenoids 52 are controlled by a microprocessor 85. The microprocessor controls the sequence of operations of each of these elements and thus the interrelated movements of (a) the table on which the assay tray is held (b) the head assembly and the various parts thereof that move vertically, and (c) actuation of the pumps to transfer liquids to and from the wells. When the machine includes means to spectrophotometrically read the liquid or solid phase in the well the microprocessor may also be used to control the spectrophotometer, record the readings made by it, process those readings or correlate them to other data, and generate reports based thereon.

As indicated previously, the apparatus shown in the drawings is designed to carry out EIAs. In EIAs one is typically looking for the presence or quantity of a multivalent antigen or hapten in a body fluid. Alternatively, EIAs may be used to look for the presence of a particular immunoglobulin in a body fluid which is indicative of a particular medical condition. In the former an immunoglobulin that is specific for (binds selectively to) the antigen/hapten of interest is immobilized on the beads. In the latter the antigen is immobilized on the bead surface. Various types of materials are used to make the beads depending upon the nature of mechanism by which the immunochemical (antibody or antigen/hapten) is affixed to the bead surface. In this regard the term "immobilization" is intended to denote the ability to hold the immunochemical by chemical (e.g., covalent bonding, hydrogen bonding) or physical mechanisms (e.g., adsorption, hydrophobic-hydrophilic affinity). Immunosorbent materials such as crosslinked dextran, agarose, silicated glass beads, polyacrylamides, polystyrene, or latex that bind the immunochemical by adsorption are commonly used. It is expected that for commercial distribution the immunochemical-bearing beads will be prepared beforehand, placed in the wells, the wells sealed such as with a strippable cover and the trays packaged for storage or shipment. The wells of a given tray may contain the same immobilized immunochemical or different immobilized immunochemicals if the tray is to be employed for different assays. Color coding or labels may be used to designate the contents of the wells and/or the assay for which they are intended.

An EIA for an antigen/hapten will typically involve the following sequence of steps.

1. Add samples and control reagents to the tray wells (and beads if they have not been pre-loaded)
2. Dilute sample with buffer (this is optional and the buffer may be added to the well before or after the sample is added)
3. Incubate well contents
4. Withdraw samples/controls from wells
5. Wash beads with buffer (typically repeated 2-5 times which involves addition and withdrawal of buffer)
6. Add enzyme-labeled antibody reagent that binds specifically to the antigen/hapten
7. Incubate
8. Withdraw enzyme-labeled antibody reagent
9. Wash beads with buffer (again, typically repeated)
10. Add substrate
11. Incubate
12. Add enzyme deactivator (optional in many assays)
13. Read wells spectrophotometrically.

Enzyme activity is related to antigen concentration and is determined by measuring the optical properties of the liquid contents of the wells at the conclusion of the assay (step 13 above) and comparing those properties to standard curves.

The invention machine would perform these steps in the following manner. The assay tray 46 preloaded with immunosorbent beads bearing the cognate antibody to the antigen/hapten is placed on table 15 at work station 47. Buffer is placed in the container 62 that feeds the first of chambers 54 (i.e., the one nearest the aspirating manifold subassembly 28). Enzyme-labeled antibody reagent, substrate, and enzyme deactivator are, respectively, placed in each of the other containers 62. Predetermined volumes of samples/controls may be loaded into a titer tray 43 at work station 39 and transferred therefrom to the wells 50 of tray 46 using the pipette subassembly as described above. After the samples and controls have been loaded into the assay tray wells the table is translated so that a row of loaded wells is below the row of dispensing tubes 56 that communicate with the dispensing manifold chamber that is interconnected to the container 62 holding the buffer. The dispensing manifold is then lowered such that the ends of those tubes are over a row of wells. The peristaltic pump 58 that serves the buffer line is then actuated to pump buffer into the dispensing manifold and out of the dispensing tubes into the wells. The samples/controls in the row of wells being worked on is thereby diluted to the desired concentration. The table is then moved to position the next row of wells beneath the buffer dispensing tubes, and the sequence is repeated to dilute sample/control in that row. Thus the sample/control in all or some of the rows may be diluted.

After the buffer dilution step the tray is incubated under conditions that permit any antigen/hapten in the sample/control to bind to the bead. If desired the machine can be equipped with a heating plate (not shown) that underlies the table 15 so that station 47 can be positioned over the heating plate to control the incubation temperature. Also, the table 15 may be translated to position the tray 46 beneath a shroud 86 to lessen the likelihood of the contents of the tray being contaminated. The table might also be agitated to facilitate mixing of the wells' contents through use of stepper motor drive 19. At the completion of the incubation, the table is translated to move the assay tray into position for the sample/control to be removed from the wells and the beads to be washed. In this operation the row of wells to be worked on is positioned beneath the aspirating tubes 66 and the first row of dispensing tubes 56 (which dispense buffer). (As indicated previously the spacing between the row of aspirating tubes and the first row of dispensing tubes is such that both rows of tubes may be received in the same row of wells). The aspirating manifold is translated downwardly to move the aspirating tubes down into the sump area of the wells (as shown in FIGS. 9 and 13). The dispensing manifold is concurrently translated downwardly to move the buffer dispensing tubes over the same wells. The peristaltic pump 69 is then activated, causing the spent sample/control to be aspirated into the aspirating manifold, and pumped therefrom into waste liquid receptacle 73. The peristaltic pump in the buffer line is then activated to pump buffer (wash liquid) into the wells, thereby washing the bead. Waste wash, buffer is withdrawn by reactivating pump 69. By alternating activation of the aspirating pump 69 and the buffer line pump as many wash cycles as desired may be made. The aspirating tubes are then withdrawn from the row of wells and the table is moved, if desired, to carry out wash operations on succeeding rows of wells.

Upon completing the washing, the table is translated to position a row of wells beneath the dispensing tubes 56 that communicate with the chamber of the dispensing manifold that is interconnected to the container 62 that holds the enzyme-labeled antibody reagent and the dispensing manifold is translated downwardly to lower those tubes into the wells. The pump in the enzyme-labeled antibody line is then activated to cause a predetermined volume of that reagent to be deposited in the wells. The dispensing manifold is then raised. This sequence is repeated to deposit labeled reagent in other rows on the tray. After the labeled reagent has been added to the wells, the tray is again incubated. Following incubation spent labeled reagent is withdrawn and the beads are washed using the same procedure that was used to withdraw spent sample/control and wash the beads previously. Substrate is then added to them by translating the table, lowering the substrate dispensing tubes into the wells and activating the pump in the substrate line. Following another incubation, enzyme deactivator is added to the wells by moving the wells into position beneath the deactivator dispensing tubes, lowering them, and activating the pump in the deactivator line.

After deactivation the optical properties of the liquid contents of the wells are read to measure enzyme activity. This may be done by removing the trays from the machine and reading the wells with standard EIA reading equipment. Alternatively, the reading step may be carried out without removing the trays as follows.

Referring to FIG. 2, the machine is equipped with spectrophotometric means for carrying out the reading step without removing the tray. This means includes a light beam generator 87 that underlies the table 15 that is capable of generating beams of light 88 and a spaced, photoelectric receiver 89 mounted on the underside of shroud 86 opposite generator 87. The table has an aperture 92 in it at station 47 such that the bottom wall of the tray beneath the wells 50 is exposed. In operation, the table is translated to position the optically flat sections of the wells' sumps between the generator and receiver, the generator is activiated to pass the beam upwardly through the liquid contents of the well to the receiver. The light energy received by the receiver may be recorded and analyzed by conventional means. The operation of the generator and receiver and the recording and analyzing of the energy received by the receiver may also be handled by microprocessor 85. Microprocessor 85 may be linked to data storage means (e.g., disk drives) and read out means (CRT displays, printers) to store the data and display it or the reports generated using it.

Other modifications of the above described embodiments of the invention that are obvious to those of skill in the fields of mechanical engineering, immunoassay devices, robotics, and related fields are intended to be within the scope of the following claims. Such modifications may include, without limitation, altering the machine so that the head assembly is horizontally movable and the table is fixed horizontally or both are moveable horizontally. Also the horizontal movement may be rotational rather than linear (e.g., the trays could be carried on a carousel with wells arranged in radial or circumferential rows). The machine might also be altered to carry out FIAs automatically. In such an embodiment the assay reading means would comprise a fluorometer which would read the fluorescence of the liquid contents of the wells. The predetermined location of the bead in the well would enable accurate and reproducible direction of the excitation energy and reading of the resulting emission energy. Further, well configurations that are conceptually similar to the embodiments described in the drawings are readily apparent, such as configurations that comprise a bead receptacle well and a separate horizontally spaced sump that is interconnected via one or more channels to permit fluid to move freely between the bead well or wells that contain screens or projections other than the illustrated posts, ramps and fins.

We claim:

1. A method of performing an automated assay in a machine having a moveable tray support, a tray having a plurality of assay wells arranged in an array of rows and columns with each assay well made of light transmitting material and configured to cause a solid phase bead to assume a position in a known area of the well and configured to have a sump region having a flat portion where the bead can never come to rest and from which sump region liquid may be withdrawn and configured such that a light beam may be passed through said flat portion with a path that will never be obstructed by said bead, and having a plurality of dispensing tubes arranged in a plurality of rows with each row coupled to its own disengaging pump and its own surface of liquid used in said assay, and having a plurality of aspirating tubes arranged in a row and coupled to an aspirating pump said aspirating tubes and said dispensing tubes being mounted on moveable platforms so as to be individually, vertically moveable comprising the steps of:

(1) placing the samples to be assayed and the appropriate control reagents in said assay wells of a tray;

(2) placing a tray at a workstation on said table wherein each assay well has placed therein an immunosorbent bead which has immobilized thereon either a specific immunoglobulin for the antigen/hapten of interest or an antigen for which the antibody of interest is specific;

(3) moving said table to register each row of wells in turn with the row of dispensing tubes coupled to a reservoir containing buffer solution and moving said dispensing tubes down into each row of assay wells in turn and activating the corresponding pump once for each row of wells for sufficient duration to pump an adequate amount of said buffer solution into all the wells;

(4) incubating the contents of said tray;

(5) moving said table to register each row of sump regions in each row of wells in turn with said row of aspirating tubes and moving said aspirating tubes down into said sump regions and activating said aspirating pump long enough for each row of wells to aspirate the samples and reagents out of each well;

(6) moving the table and platforms for said aspirating and dispensing tubes and activating said dispensing pumps and said aspirating pump appropriately to perform the following actions;

registering each row of wells in turn with the row of dispensing tubes coupled to said buffer reservoir, filling each well with buffer solution, aspirating the buffer solution out of each said well, and repeating these 3 actions a sufficient number of times to wash each said well and each said bead;

(7) moving said table and said platform for said dispensing tubes appropriately and activating the appropriate dispensing pump so as to fill each well with an enzyme labelled antibody reagent that binds specifically to the antigen/hapten bound to said bead;

(8) incubating the contents of said wells;

(9) moving said table and the platform for said aspirating tubes appropriately and activating the aspirating pump appropriately to aspirate the enzyme labelled antibody reagent out of each said well;

(10) repeating the washing actions of step 6 above;

(11) moving the table and platform for said dispensing tubes appropriately and activating the appropriate dispensing motor to fill all the wells with a substrate liquid;

(12) incubating the contents of the wells; and

(13) passing a beam of light from a spectrophotometer through said flat portion of said sump region and the liquid of each well and measuring the level of light absorption.

2. A method of performing an automated immunoassay using a machine having a moveable table and a tray having a plurality of assay wells therein where each well contains an immunosorbent bead having an antibody or antigen bound thereto and maintains the immunoabsorbent bead out of alignment with an optical analysis path, the machine further having a plurality of rows of dispensing tubes mounted on a platform which may be moved so as to move said dispensing tubes into and out of said wells, each row of said dispensing tubes being coupled through a peristaltic dispensing pump to a separate reservoir for storing various liquids, and having a row of aspirating tubes mounted adjacent to one row of said dispensing tubes close enough that said dispensing tubes and said aspirating tubes may both be lowered into the same row of wells, said row of aspirating tubes being coupled to an aspiration pump and waste receptacle and mounted on a separately moving platform which enables the aspirating tubes to be lowered into and raised out of said wells, and having a heating element under said table and a shroud over said table above said heating element comprising the steps of:

(1) filling the reservoirs for four rows of dispensing tubes with, respectively, buffer, enzyme-labelled antibody reagent, substrate and enzyme deactivator appropriate for the automated assay being performed where the buffer is loaded into the reservoir coupled to the row of dispensing tubes mounted adjacent to said row of aspirating tubes;

(2) loading each of the assay wells with sample liquid from a donor and with control reagent;

(3) moving the table to register one row of wells below the row of dispensing tubes coupled to the buffer solution reservoir and pumping buffer into the wells so registered;

(4) repeating step (3) for all the other sample containing rows of wells;

(5) moving the table over the heating element and under said shroud and controlling the heating element so as to control the temperature of the liquid in said wells for an appropriate incubation time;

(6) moving the table so that each row of sample containing wells is, in turn, registered under said row of aspirating tubes and lowering said aspirating tubes and the adjacent row of dispensing tubes into each row of wells so registered and activating the aspiration pump to pump out liquid from each said well and activating said dispensing pump to pump said buffer into said row of wells and repeating this aspirating and dispensing of buffer cycle a sufficient number of times to wash each said bead and each said well in each said row of wells;

(7) registering each row of wells below the row of dispensing tubes coupled to said reservoir containing enzyme labelled antibody and pumping same into each well;

(8) moving said table to place said tray over said heating element and under said shroud and controlling said heating element to incubate the contents of the wells;

(9) registering each row of wells under said row of aspirating tubes and lowering said aspirating tubes into each row of wells in turn and aspirating out the liquid in each said well;

(10) washing each said well using the procedure of step (6) above;

(11) registering each row of wells in turn beneath the row of dispensing tubes coupled to the reservoir containing substrate and pumping substrate into each well;

(12) moving the table to place the tray under said shroud and over said heating element and controlling said heating element to incubate the contents of said wells;

(13) registering each row of wells under the row of dispensing tubes coupled to the reservoir containing enzyme deactivator and pumping same into each well; and

(14) maintaining said bead out of alignment with said optical path and passing a beam of light through the liquid in each well along said optical path and reading the amount of light transmission through said liquid.

3. The method of claim 2 where said machine includes a spectrophotometer having a light source under said table at a predetermined position to generate beams of light up through said table toward a row of photodetectors mounted on the underside of said shroud and wherein each said well is configured so as to positively control the positive of said bead to a predetermined location under the influence of gravity and wherein step 14 comprises the steps of:

moving each row of wells in turn into registry with said light beams such that light beams pass through the liquid of said wells without being obstructed by said bead; and reading the amount of light absorption by the liquid in each well.

4. An apparatus for automatically performing immunoassays using a spectrophotometer comprising:

a spectrophotometer means for projecting a beam of light and for measuring the light intensity in said beam of light at a position removed from the position of the source of said beam of light;

a tray having a plurality of assay wells arranged in rows, each well for containing liquids needed in said assay and a solid phase having immobilized thereon a specific immunoglobulin for the antigen/hapten of interest or an antigen for which the antibody of interest is specific;

means in each assay well for preventing said solid phase from ever residing in a place in said well which would block the path of said light beam used to measure the results of said assay;

a head assembly translatable along a vertical axis;

at least one liquid aspirating manifold mounted on said head assembly having an outlet and a plurality of spaced inlets each fitted with a plurality of vertically depending liquid aspirating tubes arranged in a row with spacing to match the spacing of the rows of said assay wells;

means mounting said liquid aspirating manifold to said head assembly for moving said liquid aspirating manifold vertically even when said head assembly is not moving;

sump means in each said well for providing a location from which all the liquid in each said well may be removed by an aspirating tube at any time without interference between said solid phase and said aspirating tube;

a plurality of liquid dispensing manifolds mounted on said head assembly and having a plurality of inlets, each adapted to be connected to a source of a different liquid to be used in said assay, each said liquid dispensing manifold having a plurality of spaced outlets each fitted with a vertically depending liquid dispensing tube, the spacing between said dispensing tubes being in correspondence with the spacing between said wells of said assay tray;

a plurality of dispensing pump means each coupling one of said liquid sources to one of said liquid dispensing manifolds for pumping liquids from said source out the corresponding ones of said dispensing tubes;

an aspirating pump means coupling said aspirating manifold to waste for pumping liquids from the sump regions of any assay wells that said aspirating tubes are in;

means for moving said head assembly along its vertical axis;

a table mounted beneath said head assembly and adapted to carry said tray, said table being movable horizontally relative to said head assembly;

means for moving said table horizontally so as to position any said row of said wells in registry with any said row of dispensing tubes or with said row of aspirating tubes;

incubation means located adjacent to said table for controlling the temperature of fluid in said wells;

means for controlling each of said moving means for said head assembly and said table, said dispensing pump means, said aspirating pump means, said spectrophotometer means and said incubation means such that predetermined volumes of predetermined liquids are added to and removed from said wells in a predetermined sequence and such that the liquids in said wells are subjected to incubation times at controlled temperatures for intervals at predetermined times in said sequence and for causing said table to move said table such that each well is moved into the path of a light beam from said spectrophotometer at a predetermined time in said sequence such that said light beam passes through the liquid in said well without being blocked by said solid phase and the light absorption by said liquid is measured.

* * * * *